US00PP32506P2

(12) United States Plant Patent
McConnell

(10) Patent No.: US PP32,506 P2
(45) Date of Patent: Nov. 24, 2020

(54) ***RHODODENDRON* PLANT NAMED 'ROBLEZE'**

(50) Latin Name: *Rhododendron hybrida*
Varietal Denomination: ROBLEZE

(71) Applicant: Russell Kipling McConnell, Loxley, AL (US)

(72) Inventor: Russell Kipling McConnell, Loxley, AL (US)

(73) Assignee: PDSI, Loxley, AL (US)

( * ) Notice: Subject to any disclaimer, the term of this patent is extended or adjusted under 35 U.S.C. 154(b) by 0 days.

(21) Appl. No.: 16/602,845

(22) Filed: Dec. 10, 2019

(51) Int. Cl.
*A01H 5/02* (2018.01)
*A01H 6/36* (2018.01)

(52) U.S. Cl.
USPC ..... Plt./238
CPC ..... *A01H 6/364* (2018.05)

(58) Field of Classification Search
USPC ..... Plt./238
CPC ..... A01H 6/238
See application file for complete search history.

*Primary Examiner* — Anne Marie Grunberg
(74) *Attorney, Agent, or Firm* — Cassandra Bright

(57) ABSTRACT

A new and distinct cultivar of *Rhododendron* plant named 'ROBLEZE' is disclosed, characterized by white and coral colored flowers with a distinctive star-shape and star colored flower pattern. The new cultivar is a *Rhododendron*, suitable for ornamental garden purposes.

1 Drawing Sheet

Latin name of the genus and species: *Rhododendron hybrida.*

Variety denomination: 'ROBLEZE'.

BACKGROUND OF THE INVENTION

The new cultivar is a product of a naturally occurring branch mutation of *Rhododendron* 'Roblet', U.S. Plant Pat. No. 25,072. This new variety, hereinafter referred to as 'ROBLEZE', was discovered in April 2016 at a nursery in Loxley, Ala.

After identifying the new variety as a potentially interesting selection, the inventor first organized propagation of 'ROBLEZE' by semi-softwood cuttings during June 2016 at a nursery in Independence, La. The inventor continued controlled testing and propagation, assessing stability of the unique characteristics of this variety. Multiple generations have been reproduced and have shown that the unique features of this cultivar are stable and reproduced true to type.

SUMMARY OF THE INVENTION

The cultivar 'ROBLEZE' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'ROBLEZE' These characteristics in combination distinguish 'ROBLEZE' as a new and distinct *Rhododendron* cultivar:

1. Unique flower coloring of white with a coral colored center having a star shape.
2. Mid-sized, star-shaped single flower.
3. Spring, summer, and fall blooming.
4. Compact plant habit.
5. Good specimen plant.

6. Excellent performance in planters.
7. Very good foundation plant.
8. Does well as an understory plant in a woodland garden.
9. Hardy to Zone 7.
10. Attracts butterflies.

COMPARISON TO PARENT VARIETY

'ROBLEZE' is similar in most horticultural characteristics to the parent, however, plants of the new cultivar 'ROBLEZE' however differ in the following:

1. The new variety has different flower shape, more star-shaped than the rounded flower of the parent variety.
2. Flowers of the new variety are white with a coral center, flowers of the parent variety are coral with a thin white margin.

COMMERCIAL COMPARISON

'ROBLEZE' can be compared to the commercial variety *Rhododendron* hybrid 'Robleo', U.S. Plant Pat. No. 19,899. Plants of the new cultivar 'ROBLEZE' are similar to plants of 'Robleo' in most horticultural characteristics, however, plants of the new cultivar 'ROBLEZE' differ in the following:

1. Flowers of 'Robleze' are coral and white, flowers of 'Robleo' are medium pink with a darker pink speckled heart.
2. Plants of 'Robleze' are smaller than plants of 'Robleo'.

'ROBLEZE' can be compared to the commercial variety *Rhododendron* hybrid 'Robled', U.S. Plant Pat. No. 15,862. Plants of the new cultivar 'ROBLEZE' are similar to plants of 'Robled' in most horticultural characteristics, however, plants of the new cultivar 'ROBLEZE' differ in the following:

1. Flowers of 'Robleze' are coral and white, flowers of 'Robled' are light pink with a darker pink speckled heart.
2. Plants of 'Robleze' are smaller than plants of 'Robled'.

BRIEF DESCRIPTION OF THE PHOTOGRAPH

The accompanying photograph illustrates in full color typical flowers of the new variety. The distinctive flower shape can be seen. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'ROBLEZE' plants grown outdoors in Loxley, Ala. Plants are approximately 2 years old, in a 3 gallon nursery container. Measurements and numerical values represent averages of typical plant types.

Botanical classification: *Rhododendron hybrida* 'ROBLEZE'.

PROPAGATION

Typically by semi-hardwood cuttings in spring and summer.

Root description: Fine, fibrous young roots, well branched. Colored near RHS Grey-Brown 199A.

PLANT

Growth habit: Compact shrub. Slow to moderate growth rate.

Height: Approximately 29 cm to top of foliar and flowering plane.

Plant spread: Approximately 55 cm.

Branching characteristics: Well branched, approximately 10 to 16 primary branches from center of plant, angled approximately 45° to 75° from center of plant. Each primary branch has 4 to 7 lateral branches.

Primary branches:

Length of primary branches: Approximately 9 to 18 cm.

Diameter of primary branches: Approximately 7 mm.

Primary branch strength: Very strong, difficult to break.

Primary branch color: Near RHS Brown N200B, scales near Grey-Brown N199C. New growth near Yellow-Green 145A.

Primary branch texture: Young growth covered in appressed hairs, approximately 2 mm long, colored near Greyed-Orange 175B. Older growth scaly.

Lateral branches:

Number of lateral branches: Approximately 4 to 7 per primary branch.

Length of lateral branches: Approximately 3 to 8 cm.

Diameter of lateral branches: Average 4 mm.

Lateral branch strength: Very strong, flexible.

Lateral branch color: Near RHS Brown 200D.

Lateral branch texture: Covered in moderately dense appressed hairs, colored near RHS White 155A.

Internode length: Range between 1.0 to 3.0 cm.

Age of plant described: Approximately 2 years.

FOLIAGE

Leaf:

*Type*.—Simple.

*Arrangement*.—Alternate.

*Average length*.—3.5 to 4.0 cm.

*Average width*.—Approximately 1.6 cm.

*Shape of blade*.—Narrow spatulate to obovate. Apex broader, more spatulate on older foliage.

*Apex*.—Rounded, with a very shallow/short mucronate tip.

*Base*.—Broad attenuate.

*Attachment*.—Stalked.

*Margin*.—Entire.

*Texture of top surface*.—Leathery, hirsute. Hairs less than 1 mm.

*Texture of bottom surface*.—Glabrous, matte. Scant to moderate hirsute pubescence a long mid vein.

*Foliage scent*.—None.

*Color*.—Young foliage upper side: Near RHS Green 137C. Young foliage under side: Near RHS Yellow-Green 147C. Mature foliage upper side: Near RHS Green 139A. Mature foliage under side: Near RHS Green 138B.

*Venation*.—Type: Pinnate.

*Venation color upper side*.—Near RHS Yellow-Green N144A.

*Venation color under side*.—Near RHS Yellow-Green 144C.

Petiole:

*Length*.—About 5 mm.

*Diameter*.—Average range 1 to 2 mm.

*Color*.—Upper surface near RHS Yellow-Green N144A. Lower surface near RHS Yellow-Green 144C.

FLOWER

Bloom period: Plants begin flowering in the Spring, and continue to produce flowers throughout Summer and Fall.

Flower:

*Arrangement*.—Single, perfect, semi-open funnel shaped.

Peduncle:

*Length*.—Average 5 mm.

*Diameter*.—4 mm.

*Color*.—Near RHS Grey-Brown 199A.

*Texture*.—Densely pubescent.

*Aspect*.—Straight. Angle of attachment, approximately 45° angle from stem.

Flowers:

*Length*.—Average 4.5 cm.

*Diameter*.—Average 7.0 cm.

*Facing direction*.—Outwardly and upwardly facing.

*Persistent or self-cleaning*.—Petals self-cleaning.

*Fragrance*.—Very faint to none.

*Tube*.—Tube length: Approximately 1.5 cm. Tube width at widest point: Approximately 2.0 cm. Tube width at narrowest point: Approximately 9 mm.

Petals:

*Unfused petal segments*.—Length: Approximately 2.9 cm. Width: Approximately 3.5 cm.

*Apex*.—Retuse, irregularly notched.

*Shape of petal*.—Unfused portion, obovate.

*Petal margin.*—Entire to infrequent crenations. Ruffled aspect along margin.

*Petal arrangement.*—Approximately ⅓ fused from base.

*Petal number.*—5.

*Petal texture.*—Smooth.

*Color.*—Upper surface at first opening: Large center blotch/streak (encompassing about ⅓ to ½ of petal area) colored near RHS Red 50C, veins in this area near Red 51A. Thick margins near White 155D. White zone venation indistinguishable from white petal color. Under surface at first opening: Large center blotch/streak (encompassing about ⅓ to ½ of petal area) colored near RHS Red 50C, veins in this area near Red 51A. Thick margins near White 155D. White zone venation indistinguishable from white petal color. Inner surface at maturity: Large center star-shaped blotch/streak (encompassing about ⅓ to ½ of petal area) colored near RHS Red 51C, veins in this area near Red 51A. Thick margins near White 155D. White zone venation indistinguishable from white petal color. Outer surface at maturity: Large center blotch/streak (encompassing about ⅓ to ½ of petal area) colored near Red 55C, veins in this area near RHS Red 51A. Base Red 54B.Thick margins near White 155D. White zone venation indistinguishable from white petal color. Upper surface at fading: Large center star-shaped blotch/streak (encompassing about ⅓ to ½ of petal area) colored near RHS Red 55C, veins in this area near Red 51A. Base near Red 55B. Thick margins near White 155D. White zone venation indistinguishable from white petal color. Under surface at fading: Large center blotch/streak (encompassing about ⅓ to ½ of petal area) colored near RHS Red 55C and 55D, veins in this area near Red 51A. Base near Red 55D streaked 55B and 55C. Thick margins near White 155D. White zone venation indistinguishable from white petal color.

Bud:

*Shape.*—Elliptic.

*Length.*—3.8 cm.

*Diameter.*—1.8 cm.

*Color.*—Near RHS Red 55A, Striped White 155D.

Calyx/sepals:

*Quantity per flower.*—5 sepals.

*Shape.*—Narrow deltate.

*Length.*—5 mm.

*Width.*—3 mm.

*Apex.*—Acute.

*Base.*—Fused.

*Margin.*—Entire.

*Texture.*—Highly pubescent.

*Color.*—Inner Surface: Near RHS Yellow-Green 145A. Outer Surface: Near RHS Yellow-Green 145B.

REPRODUCTIVE ORGANS

Stamens:

*Number.*—5.

*Length.*—3.3 cm.

*Width.*—1 mm.

*Color.*—Near RHS Red 55D flushed 55C.

*Anthers.*—Length: Approximately 2 mm. Color: Near RHS Red 53A.

*Pollen.*—Not observed to date.

Pistil:

*Number.*—1.

*Length.*—3.5 cm.

*Style length.*—3.0 cm.

*Color.*—Near RHS Red 55B.

*Stigma.*—Globular, colored near Greyed-Purple 185A.

*Ovary.*—Sericeous texture. Approximately 3 mm in diameter, 5 mm long. Colored near Yellow-Green 147C. Hairs colored near White N155D.

OTHER CHARACTERISTICS

Disease and pest resistance: Not observed to be susceptible nor resistant to normal diseases and pests of *Rhododendron.*

Temperature tolerance: USDA Zone 7.

Fruit/seed production: Not observed to date.

What is claimed is:

1. A new and distinct cultivar of *Rhododendron* plant named 'ROBLEZE' as herein illustrated and described.

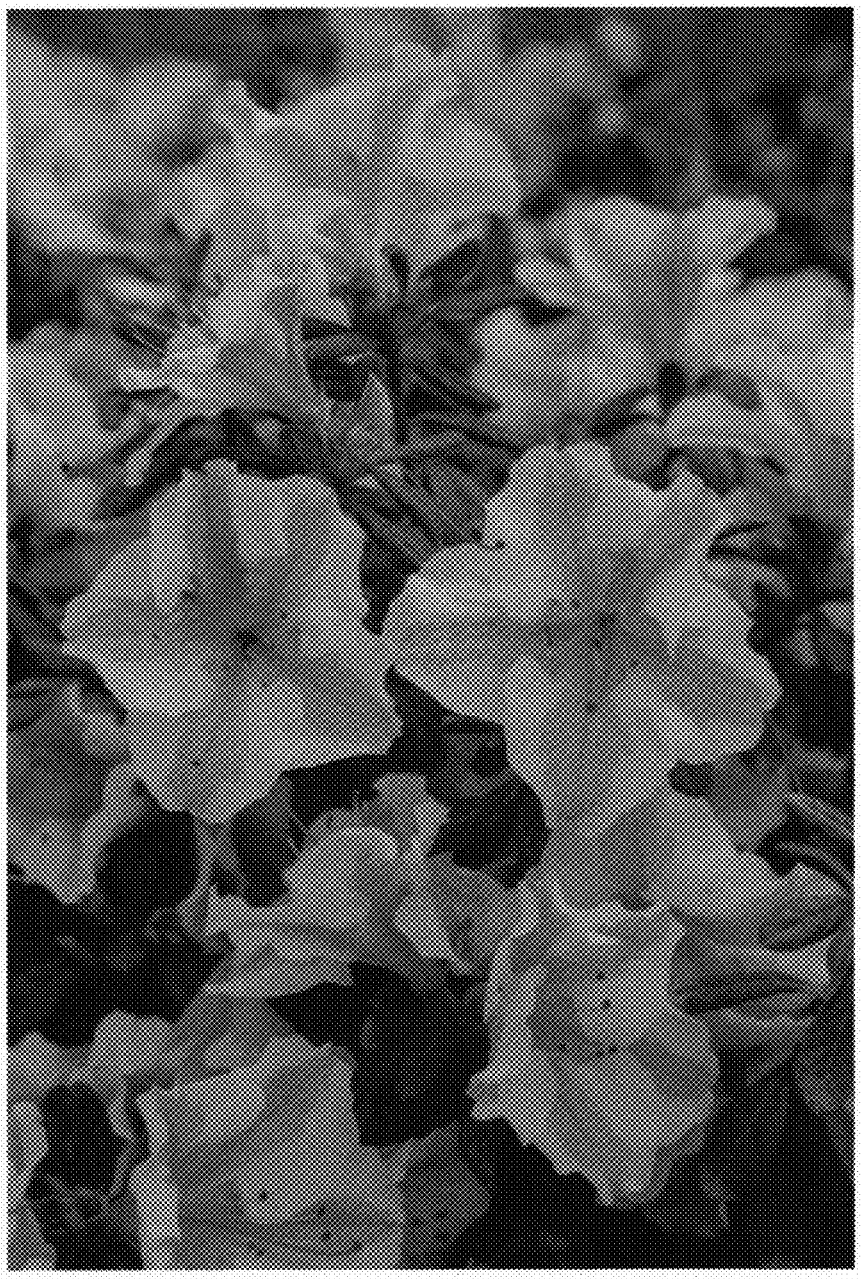

* * * * *